United States Patent [19]

Needham et al.

[11] 4,219,505
[45] Aug. 26, 1980

[54] PROCESS FOR PREPARING TETRAHALOCYCLOHEXANONE

[75] Inventors: Brian J. Needham, Newton; John Miller, Cambridge, both of England

[73] Assignee: Fisons Limited, England

[21] Appl. No.: 901,839

[22] Filed: May 1, 1978

Related U.S. Application Data

[63] Continuation-in-part of Ser. No. 745,921, Nov. 29, 1976, abandoned.

[30] Foreign Application Priority Data

May 11, 1977 [GB] United Kingdom ............... 19685/77
Nov. 24, 1977 [GB] United Kingdom ............... 48890/77

[51] Int. Cl.² .............................................. C07C 49/30
[52] U.S. Cl. .................................................... 568/348
[58] Field of Search ....................... 260/58.6 R, 593 H

[56] References Cited
U.S. PATENT DOCUMENTS

| | | | |
|---|---|---|---|
| 3,894,087 | 7/1975 | Gilbert et al. | 260/586 R |
| 3,927,106 | 12/1975 | Gilbert et al. | 260/586 R |
| 3,988,369 | 10/1976 | Pearson | 260/586 R |

Primary Examiner—Werren B. Lone
Attorney, Agent, or Firm—Wenderoth, Lind & Ponack

[57] ABSTRACT

2,2,6,6-Tetrachloro(or tetrabromo)cyclohexanone is prepared by reacting in the liquid phase chlorine or bromine with a cyclohexanone compound of formula

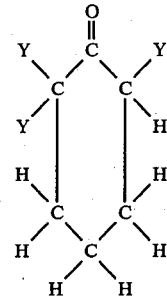

where Y is hydrogen or chlorine (to produce the tetrachloro compound) or hydrogen or bromine (to produce the tetrabromo compound) in the presence as catalyst of an organophosphorus compound of formula

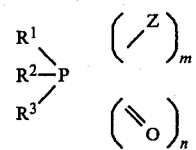

where Z is chlorine or bromine; n is 0 or 1; and when n is 0, m is 0 or 2, $R^1$ is alkyl or phenyl, and $R^2$ and $R^3$ are hydrogen, alkyl or phenyl; and when n is 1, m is 0, and $R^1$, $R^2$ and $R^3$ are the same and each is

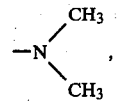

alkyl or phenyl, or $R^1$ is hydrogen and $R^2$ and $R^3$ are alkyl or phenyl;
or a salt thereof.
Each alkyl is of 1–10 carbon atoms.

12 Claims, No Drawings

PROCESS FOR PREPARING TETRAHALOCYCLOHEXANONE

This is a continuation-in-part of Ser. No. 745,921, filed Nov. 29, 1976, now abandoned.

This invention relates to a process for preparing 2,2,6,6-tetrachlorocyclohexanone or 2,2,6,6-tetrabromocyclohexanone, which are useful particularly as intermediates, e.g. in the production of pyrogallol, 1,2,3-trihydroxybenzene, or a salt thereof by hydrolysis.

Pyrogallol or its derivatives have various uses, for instance as photographic developers, in dyeing leather and wool, in the analysis of heavy metals and as intermediates e.g. in the production of the insecticide, 2,2-dimethyl-1,3-benzodioxol-4-yl methylcarbamate. At present, all the pyrogallol available in commerce is prepared by decarboxylation of gallic acid obtained from comparatively rare plant sources. This makes pyrogallol expensive and difficult to procure. Similarly pyrogallol derivatives are expensive and difficult to procure. Copending application Ser. No. 745,923—the invention of John Frederick Harris and Barrie James Magill—concerns a much improved process for the preparation of pyrogallol and certain derivatives thereof, which process avoids such rare plant sources and synthesises the product readily.

That process is for preparing a pyrogallol compound of formula

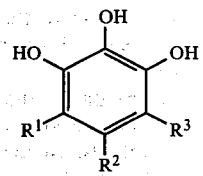

I wherein $R^1$, $R^2$ and $R^3$ are the same or different and each represents a hydrogen atom or an alkyl group of 1–6 carbon atoms, or a salt thereof,
which process comprises hydrolysing a 2,2,6,6-tetrahalocyclohexanone compound of formula

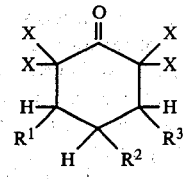

II wherein each X is the same and represents a chlorine or bromine atom; and
$R^1$, $R^2$ and $R^3$ are as defined above.

The process enables the pyrogallol compound or salt thereof to be synthesised in very high yields and in a high state of purity.

The pyrogallol compound forms salts by reason of its phenolic OH groups. The pyrogallol compound produced can be in the form of its salts. The salts include particularly alkali metal, e.g. sodium or potassium, especially sodium, salts and can be prepared from the pyrogallol compound itself in conventional ways, e.g. by reaction with alkali metal alkoxides. The pyrogallol compound itself can be prepared from its salts in conventional ways, e.g. by reaction with acid for example hydrochloric acid.

Usually the pyrogallol compound itself rather than a salt thereof is formed in the hydrolysis, and the pyrogallol compound can be converted to a salt thereof if desired though this is not preferred.

Preferably X represents a chlorine atom. The alkyl group which $R^1$, $R^2$ or $R^3$ may represent may be for example methyl, ethyl or preferably t-butyl. The hydrolysis is of particular interest where at least two of $R^1$, $R^2$ and $R^3$, preferably at least $R^1$ and $R^3$, each represents a hydrogen atom. Thus, in a particular embodiment $R^1$ and $R^3$ each represent a hydrogen atom and $R^2$ represents t-butyl. Most preferred, however, is $R^1$, $R^2$ and $R^3$ each representing a hydrogen atom, so that the pyrogallol compound or salt thereof is pyrogallol itself or a salt thereof.

The hydrolysis may be considered over all:

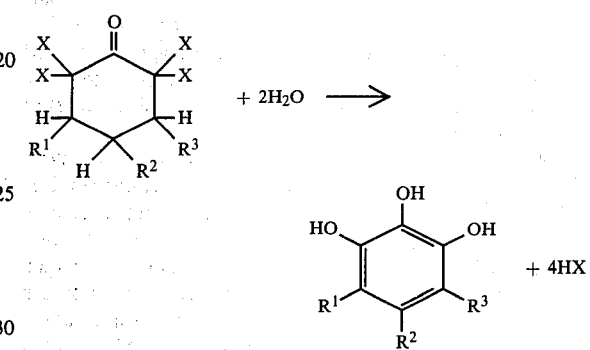

The hydrolysis can be effected directly or indirectly. Direct hydrolysis is the reaction of the tetrahalocyclohexanone compound itself with water. Indirect hydrolysis is the reaction of the tetrahalocyclohexanone compound to form a derivative which is reacted with water in a separate stage. Indirect hydrolysis can be carried out for example by reacting the tetrahalocyclohexanone compound with a metal (e.g. sodium, potassium, calcium or aluminium) alkoxide (e.g. derived from an alkanol of 1–4 carbon atoms), preferably sodium methoxide, followed by acid hydrolysis, for example by hydrochloric acid. Direct hydrolysis, however, enables the over all reaction to be conducted in a smaller number of stages, and is preferred.

The yield in the direct hydrolysis can be improved dramatically by employing a catalyst. A wide range of materials act as catalysts in this respect. There can be used as catalyst a base or an anion. An anion is included within some definitions of a base, but the present specification differentiates between them. The base can be for example morpholine, triethanolamine, cyclohexylamine, di-n-butylamine or 2-(diethylamino)ethanol or an anion exchange resin.

The catalyst is preferably, however, an anion. Suitable anions include (A) the anionic part of a cation exchange resin (e.g. a carboxylic acid cation exchange resin) in the hydrogen or salt form (e.g. the sodium, potassium, calcium or ammonium form), e.g. Amberlite IRC 50 in the hydrogen or sodium form, or, preferably, (B) an anion of another salt (called herein a simple salt to differentiate it from the ion exchange resin salt) e.g. citrate, dihydrogen citrate, hydrogen citrate, acetate, monochloroacetate, hydrogen malate, malate, hydrogen phthalate, hydrogen isophthalate, hydrogen tartrate, tartrate, oxalate ($^-$OOCCOO$^-$), o-nitrobenzoate, benzoate, lactate, propionate, glycolate, malonate ($^-$OOCCH$_2$COO$^-$), formate, salicylate (HOC$_6$H$_4$COO—), hydrogen adipate, adipate, hydrogen phosphate, dihydrogen phosphate, picolinate, furoate, dihydrogen pyrophosphate, hydrogen succinate, sulphamate, hydrogen phosphite, gluconate, borate (H$_2$BO$_3$$^-$) or fluoride.

The anion of a simple salt is preferably employed in the form of a simple salt rather than the acid. The anion catalyst can be in the form of a water-soluble metal, ammonium, or amine, salt or a mixture thereof. The amine salt can be that of a primary, secondary or tertiary amine. The amine can be aliphatic, aromatic or heterocyclic or an amine containing a mixture of such substituents on the amine nitrogen atom. It is generally preferred to use the sodium, potassium, ammonium or morpholine salt. The salt can be admixed as such or it can be generated in situ e.g. by reacting acid from which the salt is derived with alkali. For instance, cation exchange resin in the salt form can be generated in situ by providing the resin in the hydrogen form and having alkali present. Alternatively, the salt may be formed in situ by employing an ester, such as methyl oxalate, in the presence of an alkali.

Specific simple salts which are catalysts include trisodium citrate, mono-morpholine citrate, di-morpholine citrate, sodium dihydrogen citrate, disodium hydrogen citrate, sodium acetate, sodium chloroacetate, sodium hydrogen malate, disodium malate, sodium hydrogen phthalate, potassium hydrogen phthalate, ammonium hydrogen phthalate, sodium hydrogen isophthalate, sodium hydrogen tartrate, disodium tartrate, disodium oxalate, sodium o-nitrobenzoate, sodium benzoate, sodium lactate, sodium propionate, sodium glycolate, disodium malonate, sodium formate, monosodium salicylate, sodium hydrogen adipate, disodium adipate, disodium hydrogen phosphate, sodium dihydrogen phosphate, sodium picolinate, sodium furoate, disodium dihydrogen pyrophosphate, sodium hydrogen succinate, sodium sulphamate, sodium hydrogen phosphite, sodium gluconate, monosodium borate, and potassium fluoride.

In the case of a salt of a polybasic acid, a mixed salt, e.g. a sodium potassium salt, can be employed.

The anion catalyst is preferably an anion of a carboxylic acid. The carboxylic acid can be an aliphatic, aromatic, heterocyclic or alicyclic carboxylic acid. The carboxylic acid can contain one or more carboxyl groups. Where there is more than one carboxyl group, one is preferably neutralised but the others may or may not be. Where there is more than one carboxyl group, a mixed salt, e.g. a sodium potassium salt, can be employed. The carboxylic acid preferably contains only carbon, hydrogen and oxygen atoms. Especially preferred for convenience, availability and high yield it results in is (a) a straight chain alkanoic acid of 1–6 carbon atoms, which alkanoic acid is optionally substituted by one or more groups selected from carboxyl and hydroxy groups, or (b) benzoic acid substituted by one or more groups selected from carboxyl and hydroxy groups.

The pK$_a$ of the acid whose anion may be employed is usually in the range 2.0–6.5, preferably 2.8–5.7.

Particularly preferred specific salts are sodium acetate, disodium hydrogen citrate, sodium hydrogen phthalate or sodium hydrogen adipate.

A mixture of catalysts can be employed.

The direct hydrolysis occurs at a pH of at least 2. For maximum yield, the pH is preferably 2.8–6.0. The hydrolysis produces hydrohalic acid HX, which can lower the pH below these lower limits. For optimum yield it is preferred to maintain the pH above these lower limits during the hydrolysis. This can be done by employing catalyst in salt form as appropriate, e.g. as sodium salt, to raise the pH over what it would otherwise be, or by admixing alkali. The alkali can be any convenient alkali, such as alkali metal hydroxide, carbonate or bicarbonate, e.g. sodium carbonate, but preferably sodium hydroxide. Preferably the pH is maintained at 2.8–6.0 throuhout the hydrolysis.

Although we are not bound by this theory, it seems that when anion is used as catalyst, the hydrolysis may be considered in terms of one catalyst anion displacing each halogen atom X on the 2,2,6,6-tetrahalocyclohexanone compound of formula II and then each catalyst anion being itself displaced by an HO$^-$ ion from water, rearrangement occurring to result in the pyrogallol compound of formula I. It can be seen that this is analogous to the indirect hydrolysis mentioned above in which the tetrahalocyclohexanone compound is reacted with a metal alkoxide and the product is acid hydrolysed; there an alkoxide ion is the anion to displace each X atom, and the displacement of the alkoxide ion occurs in a separate stage.

When an anion is used as catalyst and the anion is that of a simple salt, the amount of catalyst is preferably at least 4 anions per molecule of tetrahalocyclohexanone. Better yields are generally obtained using 6–10 of the catalyst anions, than using 4 of the catalyst anions, per molecule of tetrahalocyclohexanone. Generally, no better yield is obtained using 16 of the catalyst anions than using 8 of the catalyst anions, per molecule of tetrahalocyclohexanone.

When an anion is used as catalyst and the anion is that of a cation exchange resin, the amount of catalyst is preferably at least 4 equivalents, especially 6–10 equivalents, of anion per mole of tetrahalocyclohexanone, generally no better yield being obtained using 16 rather than 8 equivalents of anion per mole of tetrahalocyclohexanone.

When a base is used as catalyst, it is thought, though we are not bound by this theory, that one equivalent of base reacts with one equivalent of hydrohalic acid produced in the hydrolysis. When a base is used as catalyst, the amount of catalyst is preferably at least 4 equivalents of base per mole of tetrahalocyclohexanone.

When the direct hydrolysis is used, an organic liquid, e.g. methanol or ethanol, may be employed in the reaction mixture to give a system which is initially of one phase rather than two phases.

The hydrolysis is preferably conducted in solution. At least the theoretical quantity of water to effect the hydrolysis must be employed, and when direct hydrolysis is employed, the solvent is preferably water in excess of that required for hydrolysis. When direct hydrolysis is employed, preferably the whole of any catalyst is in solution.

When the alkoxide route mentioned above is employed, the reaction with the alkoxide is generally conducted in the presence as solvent of the alkanol from which the alkoxide is derived, and the subsequent acid hydrolysis may be conducted in the presence as solvent of water in excess of that required for hydrolysis.

Preferably the hydrolysis employs 0.3 ml–1 liter of water per gram of tetrahalocyclohexanone compound.

The hydrolysis may for example be conducted at a temperature of 0°–250° C. e.g. 0°–120° C. The reaction mixture is usually heated. In a preferred embodiment, particularly when direct hydrolysis is employed, the temperature is 60°-140° C. Preferably direct hydrolysis is conducted under reflux.

The hydrolysis may be conducted under a pressure which is above, at, or below atmospheric pressure. The pressure may for instance be 0.1-15 atmospheres, conveniently atmospheric pressure.

The pyrogallol compound and its salts absorb oxygen when hot and the salts absorb oxygen even at ambient temperature. Accordingly, excessive heating of them should be avoided and it may be desirable in some instances to conduct the hydrolysis under an inert atmosphere, e.g. an atmosphere of nitrogen or carbon dioxide.

The product can be isolated and purified in conventional ways.

The starting material of formula II in the above process can be prepared in known ways or in ways known for analogous compounds. When it is 2,2,6,6-tetrachlorocyclohexanone or 2,2,6,6-tetrabromocyclohexanone, it can be prepared by chlorinating or brominating cyclohexanone. Alternatively, 2,2,6,6-tetrachlorocyclohexanone can be prepared by chlorinating cyclohexanol. 2,2,6,6-tetrachlorocyclohexanone or 2,2,6,6-tetrabromocyclohexanone is preferably prepared, however, by a process which is surprisingly useful and which is the subject of the present invention.

Accordingly, the invention provides a process for preparing 2,2,6,6-tetrachlorocyclohexanone or 2,2,6,6-tetrabromocyclohexanone, which comprises reacting in the liquid phase, in the case of the production of 2,2,6,6-tetrachlorocyclohexanone, chlorine, and in the case of the production of 2,2,6,6-tetrabromocyclohexanone, bromine, with a cyclohexanone compound of formula

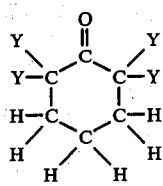

III where each Y is the same or different and represents, in the case of the production of 2,2,6,6-tetrachlorocyclohexanone, an atom of hydrogen or chlorine, and in the case of the production of 2,2,6,6-tetrabromocyclohexanone, an atom of hydrogen or bromine, in the presence as catalyst of an organophosphorus compound of formula

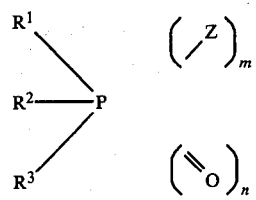

IV where Z represents an atom of chlorine or bromine; n is 0 or 1; and when n is 0, m is 0 or 2, $R^1$ is alkyl of 1 to 10, e.g. 1 to 6, carbon atoms or phenyl, and $R^2$ and $R^3$ are the same or different and are hydrogen, alkyl of 1 to 10, e.g. 1 to 6, carbon atoms or phenyl; and when n is 1, m is 0, and $R^1$, $R^2$ and $R^3$ are the same and each is

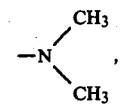

alkyl of 1 to 10, e.g. 1 to 6, carbon atoms or phenyl, or $R^1$ is hydrogen and $R^2$ and $R^3$ are the same or different and each is alkyl of 1 to 10, e.g. 1 to 6, carbon atoms or phenyl;

or a salt of such an organophosphorus compound.

This catalyst enables the reaction to be carried out readily and in high yield. It is particularly useful when the desired product of the reaction is to be hydrolysed to pyrogallol or a salt thereof, and especially when the pyrogallol or salt thereof is to be reacted with 2,2-dimethoxypropane and the 2,2-dimethyl-4-hydroxy-1,3-benzodioxole product reacted with methyl isocyanate to produce the pesticide bendiocarb, 2,2-dimethyl-1,3-benzodioxol-4-yl methylcarbamate.

Any alkyl group in the catalyst is usually of 1-4 carbon atoms, particularly methyl, ethyl or n-butyl, though it may also be of 8 carbon atoms especially 2-ethylhexyl or n-octyl. When there is more than one alkyl group in the molecule, they are conveniently the same.

In a preferred embodiment, n is 1 and $R^1$, $R^2$ and $R^3$ are each

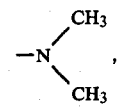

i.e. the catalyst is hexamethylphosphoramide or a salt thereof.

The catalyst is preferably a tertiary phosphine, e.g. dimethylethylphosphine, trin-n-octylphosphine or tri(2-ethylhexyl)phosphine, or a salt thereof. In a preferred embodiment, the catalyst is tributylphosphine. References to tributylphosphine are to tri-n-butylphosphine. In another preferred embodiment, the catalyst is tributylphosphine or a salt thereof. In a further embodiment, the catalyst is other than tributylphosphine. In another embodiment, the catalyst is other than ributylphosphine or a salt thereof.

The catalyst may be a phosphine oxide, particularly a tertiary phosphine oxide.

In a preferred embodiment, the catalyst is triphenylphosphine or triphenylphosphine oxide.

In a particular embodiment, m is 0.

The catalyst may be provided as the organophosphorus compound itself or as a salt of this compound where a salt exists. Thus, the reaction may be carried out in the presence of acid salts of the catalysts. Suitable acids include both inorganic acids, such as Lewis acids (e.g. boron trifluoride) or mineral acids e.g. hydrochloric or sulphuric acid, or organic acids, such as carboxylic acids containing up to 10 carbon atoms (e.g. acetic acid or propionic acid). The salt may be a quaternary phosphonium salt.

The nature of the acid portion of the salt is not particularly significant; it is the basic portion of the catalyst which is important. Moreover, copious quantities of hydrochloric or hydrobromic acid (depending on whether chlorine or bromine is used) are normally produced in the course of the reaction, so that a substantial portion of the catalyst is generally present as the hydrochloric or hydrobromic acid salt regardless of the particular ingredient used as source of the catalyst.

Preferably 2,2,6,6-tetrachlorocyclohexanone is prepared and the catalyst is provided in the form of the hydrochloric acid salt, e.g. tributylphosphine hydrochloride or triphenylphosphine hyrochloride. Conveniently hydrogen chloride gas is passed into tributylphosphine or triphenylphosphine in 2,2,6,6-tetrachlorocyclohexanone or carbon tetrachloride, and the salt formed used as catalyst in the chlorination to produce 2,2,6,6-tetrachlorocyclohexanone.

The catalyst may be chlorinated or brominated during the course of the reaction, and the acid portion of the acid salt catalyst, particularly salts of organic acids, may be chlorinated or brominated during the course of the reaction. Thus, if the catalyst is provided as a phosphine (n is 0 in the formula above), it may well be chlorinated to and function as the dichloro derivative. For instance, tributylphosphine or triphenylphosphine may be converted to and function as $Bu_3PCl_2$ or $Ph_3PCl_2$ respectively. The catalyst may be provided as such a chlorinated or brominated derivative. In the case of chlorination with tributylphosphine or triphenylphosphine, however, this is not preferred since the dichloro derivatives tend to be unstable.

When the catalyst is provided as a phosphine (n is 0 in the formula above), it may well be oxidised during the course of the reaction to and function as a phosphine oxide (n is 1 in the formula above). For instance, if the catalyst is provided as tributylphosphine or triphenylphosphine or a salt of either, it may well be chlorinated to the corresponding dichloro derivative and then oxidised to the corresponding tributylphosphine oxide or triphenylphosphine oxide. The catalyst may be provided as such a phosphine oxide.

Preferably the catalyst is provided to the reaction mixture as an organophosphorus compound of formula II wherein m is 0 or a salt thereof.

Especially preferred is providing the catalyst to the reaction mixture as tributylphosphine or a salt thereof, triphenylphosphine or a salt thereof, tributylphosphine oxide or triphenylphosphine oxide. References to tributylphosphine oxide are tri-n-butylphosphine oxide.

The catalyst may be a mixture of the organophosphorus compounds but this is not preferred.

The amount of catalyst is not critical, but generally its weight is at least 0.1%, preferably from 0.5 to 12%, of the weight of the cyclohexanone compound.

The compounds of formula III employed as starting materials in the process are either known compounds, or may be prepared by methods welll known to those skilled in organic chemical synthesis for the preparation of analogous compounds.

The process is of particular interest for the production of 2,2,6,6-tetrachlorocyclohexanone, so that the halogen involved is chlorine rather than bromine and Y represents an atom of hydrogen or chlorine rather than an atom of hydrogen or bromine.

The cyclohexanone compound is preferably cyclohexanone itself, though an intermeidately halogenated compound can be employed. For instance, to produce 2,2,6,6-tetrachlorocyclohexanone one can start from 2,2,6-trichlorocyclohexanone.

The reaction is preferably conducted in the presence of a solvent. Suitable solvents include saturated chlorinated hydrocarbons (e.g. aliphatic hydrocarbons containing 1 or 2 carbon atoms and 2-4 chlorine atoms, such as carbon tetrachloride, methylene dichloride, 1,2-dichloroethane or tetrachloroethanes), saturated hydrocarbons (e.g. those containing 5-10 carbon atoms such as pentane, hexane, cyclohexane, octane or decane) or saturated carboxylic acids (e.g. saturated aliphatic carboxylic acids containing 2-5 carbon atoms, such as acetic acid, propionic acid or butanoic acid). In the production of 2,2,6,6-tetrachlorocyclohexanone, 2,2,6-trichlorocyclohexanone may be employed as solvent. Preferably, however, the solvent is molten desired product, e.g. 2,2,6,6-tetrachlorocyclohexanone, itself. A mixture of solvents can be employed but this is not preferred.

In a preferred mode of operation, the halogen and cyclohexanone compound are fed to a reaction zone containing a solvent and the catalyst.

The reaction is usually conducted at a temperature within the range 60°-160° C., preferably 75°-110° C., e.g. 80°-110° C. The reaction temperature is preferably below the boiling point of the solvent if a solvent is employed. When molten 2,2,6,6-tetrachlorocyclohexanone is employed as solvent, the minimum reaction temperature is its melting point as altered by the other materials present. The melting point of pure 2,2,6,6-tetrachlorocyclohexanone is 82°-83° C.

When chlorinating cyclohexanone itself, the first 3 chlorine atoms may be introduced to the molecule, to produce 2,2,6-trichlorocyclohexanone, at a lower temperature, e.g. down to 20° C., but to introduce the fourth chlorine atom, to produce 2,2,6,6-tetrachlorocyclohexanone, the temperature is usually as discussed above.

In the present reaction, water is preferably avoided. The weight of water is preferably below 5% of the weight of the cyclohexanone compound. The reaction is preferably carried out under substantially anhydrous conditions, i.e less than 1%, preferably less than 0.5%, by weight of water being present based on the weight of the cyclohexanone compound.

Preferably, 2,2,6,6-tetrachlorocyclohexanone is prepared by reacting chlorine with cyclohexanone, in the liquid phase, under substantially anhydrous conditions, at a temperature of 60°-160° C., in a process in which there is provided as catalyst for the reaction an organophosphorus compound of formula

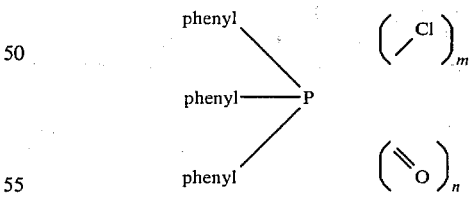

wherein n is 0 or 1; and
when n is 0, m is 0 or 2 and when n is 1, m is 0;
or a salt of such an organophosphorus compound.

The overall amount of chlorine or bromine employed is normally sufficient to convert all the cyclohexanone compound to desired product. When the reaction is conducted by feeding the halogen and cyclohexanone compound to a reaction zone containing a solvent and the catalyst, it is preferred, in order to minimise side reaction, that the amount of the halogen in contact with the cyclohexanone in the reaction zone be at all times at least the stoichiometric amount required to convert the cyclohexanone compound present to the desired product. For instance, starting from cyclohexanone there is preferably at least 4 moles of halogen fed per mole of cyclohexanone fed; desirably, 4-6 moles of halogen are fed while each mole of cyclohexanone is fed.

The desired product can be separated in conventional ways. It can be used without purification to produce pyrogallol or a salt thereof by hydrolysis, but the product can be purified if desired by conventional techniques e.g. by recrystallisation or sublimation. The hydrolysis is described for example in copending application Ser. No. 745,923.

The invention is illustrated by the following Examples, in which parts and percentages are by weight.

EXAMPLE 1

A mixture of 2,2,6,6-tetrachlorocyclohexanone (100 parts) and water (532 parts) was heated to 60° C. and morpholine (149 parts) added dropwise over a period of 14 mins. The mixture was maintained at 60° C. for a further 4 mins, then cooled and filtered. The filtrate was acidified by addition of 21 parts of concentrated hydrochloric acid solution, then continuously extracted with ether. After drying over $MgSO_4$, the extract was evaporated to give 21 parts of tar, shown to contain 6 parts (11.2% yield) of pyrogallol by GLC (gas liquid chromatography) after acetylation.

EXAMPLE 2

Under a blanket of nitrogen were mixed 2,2,6,6-tetrachlorocyclohexanone (100 parts), sodium acetate (424 parts) and water (1,059 parts), and the mixture refluxed for 10 minutes. The mixture was then cooled to 50° C. when sodium bicarbonate (318 parts) was added giving severe foaming. The mixture was then extracted continuously with ether, the extract dried over magnesium sulphate and evaporated to give a residue (39 parts). The residue was triturated with chloroform (39 parts) to give after filtering and drying in air 15.2 parts of pyrogallol (28.5% yield) as a tan solid, m.pt. 130.5°-133.5° C.

EXAMPLE 3

Under a blanket of nitrogen were mixed 2,2,6,6-tetrachlorocyclohexanone (100 parts), disodium oxalate (456 parts) and water (1,064 parts), and the mixture refluxed for two hours. The mixture was then extracted continuously with ether and dried over sodium sulphate. After filtering, the extract was evaporated to give 52.2 parts of residue shown to contain pyrogallol (24.5 parts, 46% yield) by GLC after conversion to the triacetate.

EXAMPLE 4

2,2,6,6-Tetrachlorocyclohexanone (2.36 g, 0.01 M) was added to 35 mls of a stirred 27% sodium methoxide solution (0.17 M) under nitrogen at 24° C. The temperature of the mixture rose and was held at 45° C. by external cooling. When the exotherm had finished, the mixture was cooled in ice and concentrated hydrochloric acid (17 mls) and water (28 mls) were added. The methanol was distilled from the reaction mixture under nitrogen, and the resultant aqueous solution was continuously extracted with ether. The ether extract was dried ($MgSO_4$) and the ether removed under vacuum to give a residue (0.85 g) analysing as 18% pyrogallol. This represents a pyrogallol yield of 12.2%.

EXAMPLE 5

2,2,6,6-Tetrachlorocyclohexanone (4.72 g, 0.02 M) was added to a solution of disodium hydrogen citrate (0.16 M) made by adding with cooling sodium hydroxide (12.8 g) to a solution of citric acid monohydrate (33.6 g) in water (50 mls). The mixture was stirred and heated to reflux. The reaction mixture was sampled at intervals and analysed for free chloride until the samples showed the reaction was complete. The total reflux time was 4 hours. The reaction mixture was continuously extracted with ether. The ether extract was dried ($MgSO_4$), filtered and the ether removed to give a residue (2.74 g) analysing as 77.5% pyrogallol. The pyrogallol yield is 84.4%.

EXAMPLE 6

2,2,6,6-Tetrachlorocyclohexanone (4.72 g, 0.02 M) was added to a mixture of phthalic acid (26.5 g, 0.16 M) in water (74 mls) to which sodium hydroxide (6.4 g, 0.16 M) had been added. The mixture was heated to reflux for 1½ hours. Sodium hydroxide solution (5 mls of 5 N) was added over 5 minutes and the mixture was heated at reflux for a further 2½ hours. A sample was analysed for free chloride and this indicated the reaction was complete. Concentrated hydrochloric acid (13 mls) was added at 90° C. The reaction mixture was cooled to 5° C. and the phthalic acid was removed by filtration. The pH of the filtrate was adjusted to 3.5 and it was continuously extracted with ether. The ether extract was dried ($Na_2SO_4$), filtered and the ether removed to give crude product (3.04 g) which contained 2.02 g of pyrogallol. This represents a pyrogallol yield of 80%.

EXAMPLE 7

Glacial acetic acid (9.6 g, 0.16 M) was dissolved in distilled water and the pH was adjusted to 4.7 with 10 N sodium hydroxide solution. The volume of the solution was adjusted to 55 mls by dilution with distilled water. 2,2,6,6-Tetrachlorocyclohexanone (4.72 g, 0.02 M) was added and the mixture was heated to reflux. The pH of the reaction mixture was kept at 4.7 by the addition of 5 N sodium hydroxide solution. Samples were taken intermittently and analysed for free chloride to determine the end of reaction. The resulting aqueous solution was continuously extracted with ether. The ether extract was dried ($Na_2SO_4$), filtered and the ether removed to give crude product (3.5 g) which contained 1.46 g of pyrogallol. The pyrogallol yield was 58%.

EXAMPLE 8

Amberlite IRC 50 ion exchange resin in the sodium form (16.8 g, dry) was suspended in distilled water (50 mls). 2,2,6,6-Tetrachlorocyclohexanone (4.72 g, 0.02 M) was added and the mixture was heated to reflux for 1½ hours by which time the pH had fallen from 6.2 to 1.7. The pH was adjusted to 3.8 and reflux was continued for a further 4 hours during which the pH was kept between 2 and 4 by the addition of 5 N sodium hydroxide solution. A chloride analysis indicated 92% completion of the hydrolysis. The resin was filtered off and the reaction mixture was continuously extracted with ether. The ether extract was dried, filtered, and the ether removed to leave a brown oil (1.2 g). This analysed as 19.6% pyrogallol, representing a 9.3% pyrogallol yield.

EXAMPLE 9

2,2,6,6-Tetrachlorocyclohexanone (4.72 g, 0.02 M) was added to distilled water (50 mls) and the pH was adjusted to 5.0 with 5 N sodium hydroxide solution. The mixture was stirred and heated to reflux and the pH was kept at 5.0 by the addition of sodium hydroxide solution. The mixture was sampled at intervals and analysed for free chloride until the reaction was complete. The reaction mixture was ether extracted and the ether extract was dried ($Na_2SO_4$), filtered and the ether distilled off to give a brown oil (1.3 g). This contained 0.03 g of pyrogallol which represents a 1.2% yield.

EXAMPLE 10

Following Example 9 but maintaining the pH at 3.0 gave a 3.7% yield of pyrogallol.

EXAMPLE 11

Following Example 5 but using 0.02 moles of 2,2,6,6-tetrabromocyclohexanone instead of the tetrachlorocyclohexanone gave a 44% yield of pyrogallol.

EXAMPLES 12-52

A suspension of 2,2,6,6-tetrachlorocyclohexanone (4.72 g, 0.02 M) was heated under reflux with an aqueous solution/suspension of the catalyst compound listed below (0.16 M; in the case of the Amberlite IRC 50, 16.0 g of dry resin were employed) in 50 mls of water. The mixture was sampled at intervals and analysed for free chloride to determine the end point of the reaction. The aqueous reaction mixture was then filtered if necessary and extracted continuously with ether. The ether extract was dried ($Na_2SO_4$), filtered and the ether removed to give the crude pyrogallol. This was analysed to determine the yield.

| Ex. | Catalyst Compound | Yield of Pyrogallol, % |
| --- | --- | --- |
| 12 | Trisodium Citrate | 25.5 |
| 13 | Sodium Dihydrogen Citrate | 31.0 |
| 14 | Sodium Chloroacetate | 31.0 |
| 15 | Sodium Hydrogen Malate | 71.0 |
| 16 | Disodium Malate | 52.0 |
| 17 | Potassium Hydrogen Phthalate | 75.0 |
| 18 | Ammonium Hydrogen Phthalate | 52.0 |
| 19 | Sodium Hydrogen Isophthalate | 59.8 |
| 20 | Sodium Hydrogen Tartrate | 58.0 |
| 21 | Disodium Tartrate | 60.5 |
| 22 | Disodium Oxalate | 44.0 |
| 23 | Sodium-o-Nitrobenzoate | 35.1 |
| 24 | Sodium Benzoate | 49.5 |
| 25 | Sodium Lactate | 68.5 |
| 26 | Sodium Propionate | 42.9 |
| 27 | Sodium Glycolate | 57.0 |
| 28 | Disodium Malonate | 27.0 |
| 29 | Sodium Formate | 20.8 |
| 30 | Sodium Salicylate | 29.0 |
| 31 | Sodium Hydrogen Adipate | 82.0 |
| 32 | Disodium Adipate | 46.0 |
| 33 | Amberlite IRC 50 $H^+$ form | 17.0 |
| 34 | Disodium Hydrogen Phosphate | 22.6 |
| 35 | Sodium Dihydrogen Phosphate | 32.5 |
| 36 | Monosodium Borate | 7.0 |
| 37 | Potassium Fluoride | 16.0 |
| 38 | Ethylene Diamine Tetraacetic acid, Disodium Salt | 49.0 |
| 39 | Sodium Hydrogen Fumarate | 53 |
| 40 | Disodium Fumarate | 58 |
| 41 | Sodium Hydrogen 1,2,3,6-Tetra hydrophthalate | 62 |
| 42 | Sodium Hydrogen Maleate | 34 |
| 43 | Sodium Pivalate | 11 |
| 44 | Dipotassium Oxalate | 71 |
| 45 | Sodium Picolinate | 6 |
| 46 | Sodium Furoate | 19 |
| 47 | Disodium Di Hydrogen Pyrophosphate | 47 |
| 48 | Sodium Hydrogen succinate | 76 |
| 49 | Sodium sulphamate | 13 |
| 50 | Sodium Hydrogen phosphite | 18 |
| 51 | Dimethyl oxalate | 25 |
| 52 | Sodium gluconate | 67 |

EXAMPLE 53

2,2,6,6-Tetrachlorocyclohexanone (4.72 g, 0.02 M) was added to a solution of morpholine citrate made by adding with cooling morpholine (24.6 mls 0.283 moles) to a solution of citric acid monohydrate (33.6 g, 0.16 M) in water (50 mls). The mixture was stirred and heated to reflux. The reaction mixture was sampled at intervals and analysed for free chloride until the samples showed the reaction was complete. The total reflux time was 3 hours. The reaction mixture was continuously extracted with ether. The ether extract was dried ($MgSO_4$), filtered and the ether removed to give a residue (5.4 g) analysing as 33.6% pyrogallol. The pyrogallol yield is 71.9%.

EXAMPLE 54

2,2,6,6-Tetrachloro-4-methylcyclohexanone (5.0 g, 0.02 M) was added to a solution of sodium hydrogen phthalate (30.1 g, 0.16 M) in 50 mls of water. The mixture was heated at reflux and sampled at intervals for free chloride determination. When the reaction was complete the mixture was cooled, filtered, ether extracted and the ether removed to give a crude product, 3.8 g, which contained 1,2,3-trihydroxy-5-methylbenzene (methyl pyrogallol). (1.26 g). This represents a 45% yield.

EXAMPLE 55

45 g of 2,2,6,6-tetrachlorocyclohexanone (TCCH) and 5 g of tributyl phosphine were charged to a 500 ml flask fitted with a mechanical stirrer, a thermometer, a water condenser and a chlorine inlet tube having a sinter outlet to the bottom of the flask. The flask was heated, and the melt at 85°-90° C. was swept with nitrogen for 10 minutes. At 95°-105° C., 276 g of chlorine and 66 g of cyclohexanone were charged to the flask continuously over 6.7 hours. The mole ratio of chlorine to cyclohexanone was kept at 5.8 throughout the addition. Chlorine was then added continuously at the same rate as it was before for 1½ hours while maintaining the same temperature. 375 ml n-hexane were added to the reaction mixture, which was then heated to give a clear solution.

Cooling of the solution to 5° C. precipitated crystals of TCCH, which after filtration and drying contained 137.0 g (86.5% yield) of freshly formed TCCH (i.e. the TCCH over and above that charged initially to the flask). Analysis showed that the resultant TCCH was 99% pure.

EXAMPLE 56

5.0 g Triphenylphosphine were added to 60 mls $CCl_4$ in a 250 mls flask fitted with a stirrer, condenser, thermometer, gas inlet tube below the liquid surface and cyclohexanone feed tube above the liquid surface. HCl gas equivalent to the triphenylphosphine was bubbled in at room temperature followed by a nitrogen purge while the mixture was heated to reflux. Cl₂ gas, 3.48 moles, and cyclohexanone, 0.695 mole, were then fed in at even rates over 4.25 hours, while the temperature of the reaction mixture rose from 70°–105° C. The cyclohexanone feed was then stopped and the Cl₂ feed continued at the same rate for a further 1.5 hours. The resulting clear solution crystallised on cooling to 191.3 g of a white solid containing 81% of TCCH (94.5% of theoretical yield).

EXAMPLE 57

As Example 56, but with 0.5 g instead of 5.0 g of triphenylphosphine. TCCH yield was 71.8%.

EXAMPLE 58

As Example 57, but omitting HCl. TCCH yield was 59.3%.

EXAMPLE 59

As Example 56, substituting 5.0 g triphenylphosphine oxide for triphenylphosphine. TCCH yield was 99%.

EXAMPLE 60

As Example 59, but using 0.5 g instead of 5.0 g of triphenylphosphine oxide. TCCH yield was 68.7%.

EXAMPLE 61

As Example 56 substituting 5 g hexamethylphosphoramide for the triphenylphosphine. TCCH yield was 91.2%.

EXAMPLE 62

As Example 56 but omitting triphenylphosphine and HCl. TCCH yield was 4.6%.

EXAMPLES 63–65

Following the general procedure of Example 55, chlorine and cyclohexanone, in a mole ratio of 5:1, were fed into carbon tetrachloride as solvent containing either no catalyst or the catalyst listed in the table below in amount equal to 7% of the weight of total cyclohexanone feed. The feed of chlorine and cyclohexanone was maintained for 4.3 hours, and in the case of the catalyst the feed of chlorine only was then continued at its same rate for another 1.5 hours. The results are shown in the following table:

| Example | Catalyst | TCCH % yield | % TCCH in product At end of joint feed | After post feed chlorination |
|---|---|---|---|---|
| 63 | None | 7 | | |
| 64 | Tributyl-phosphine hydrochloride | 95 | 49 | 78 |
| 65 | Triphenyl-phosphine | 95 | | |

We claim:
1. A process for preparing a tetrahalocyclohexanone compound of formula

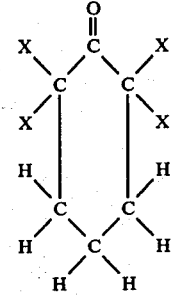

where each X is the same and represents a chlorine or bromine atom, which process comprises reacting in the liquid phase X₂, where X is as defined above, with a cyclohexanone compound of the formula

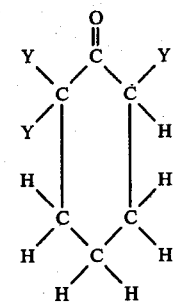

where each Y is the same or different and represents a hydrogen atom or X, in the presence as catalyst of

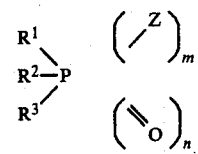

where Z represents an atom of chlorine or bromine; n is 0 or 1; and when n is 0, m is 0 or 2, R¹ is alkyl of 1 to 10 carbon atoms or phenyl, and R² and R³ are the same or different and are hydrogen, alkyl of 1 to 10 carbon atoms or phenyl; and when n is 1, m is 0, and R¹, R² and R³ are the same and each is

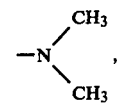

alkyl of 1 to 10 carbon atoms or phenyl, or R¹ is hydrogen and R² and R³ are the same or different and each is alkyl of 1 to 10 carbon atoms or phenyl; or a salt of such an organophosphorus compound, at a temperature of 60° to 160° C.

2. A process according to claim 1 wherein the catalyst is tributylphosphine.

3. A process according to claim 1 wherein n is 1 and R¹, R² and R³ are each

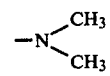

4. A process according to claim 1 wherein $R^1$, $R^2$ and $R^3$ are each phenyl.

5. A process according to claim 1 wherein m is 0.

6. A process according to claim 1 wherein 2,2,6,6-tetrachlorocyclohexanone is prepared.

7. A process according to claim 1 wherein the cyclohexanone compound is cyclohexanone itself.

8. A process according to claim 1 wherein the reaction is conducted under substantially anhydrous conditions.

9. The process according to claim 6 wherein the amount of halogen in contact with the cyclohexanone in said reaction zone is at all times at least the stoichiometric amount required to convert said cyclohexanone compound to said tetrahalocyclohexanone compound.

10. The process according to claim 9 wherein 4 moles of halogen per mole of cyclohexanone are employed.

11. The process according to claim 10 wherein 4 to 6 moles of halogen per mole of cyclohexanone are employed.

12. A process for preparing 2,2,6,6-tetrachlorocyclohexanone, by reacting in the liquid phase, under substantially anhydrous conditions, at a temperature of 60°–160° C., chlorine with cyclohexanone, in which process there is provided as catalyst for the reaction an organophosphorus compound of formula:

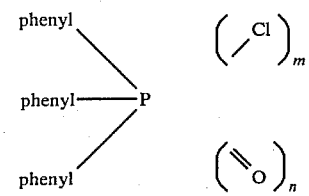

wherein n is 0 or 1; and
when n is 0, m is 0 or 2 and when n is 1, m is 0;
or a salt of such an organophosphorus compound.

* * * * *